(12) United States Patent
Uen et al.

(10) Patent No.: US 8,478,540 B2
(45) Date of Patent: Jul. 2, 2013

(54) METHOD AND APPARATUS FOR PRODUCING MINERAL WATER

(75) Inventors: Tzu-Wen Uen, Miaoli (TW); Shu-Fei Chan, Miaoli (TW); Chen-Neng Chen, Miaoli (TW); Yan-Yng Shen, Miaoli (TW)

(73) Assignee: Aqua Lohas Water-Tech Services Co., Ltd., Jhunan, Miaoli (TW)

( * ) Notice: Subject to any disclaimer, the term of this patent is extended or adjusted under 35 U.S.C. 154(b) by 574 days.

(21) Appl. No.: 12/702,863

(22) Filed: Feb. 9, 2010

(65) Prior Publication Data
US 2011/0159150 A1   Jun. 30, 2011

(30) Foreign Application Priority Data
Dec. 29, 2009   (CN) .......................... 2009 1 0252560

(51) Int. Cl.
*G01N 33/48* (2006.01)
*A23L 1/304* (2006.01)

(52) U.S. Cl.
USPC ............................................. 702/19; 426/74

(58) Field of Classification Search
None
See application file for complete search history.

(56) References Cited

U.S. PATENT DOCUMENTS

| | | | |
|---|---|---|---|
| 3,785,492 A | 1/1974 | Mazza | |
| 2005/0113649 A1 * | 5/2005 | Bergantino | 600/300 |
| 2005/0133420 A1 | 6/2005 | Rinker | |
| 2006/0191824 A1 | 8/2006 | Arett | |
| 2009/0173616 A1 | 7/2009 | Cabados | |

FOREIGN PATENT DOCUMENTS

| | | |
|---|---|---|
| JP | 2009-245171 A | 10/2009 |
| WO | WO 02/085794 A1 | 10/2002 |
| WO | WO 03/050045 A1 | 6/2003 |
| WO | WO 2005/115922 A1 | 12/2005 |
| WO | WO 2008/004899 A2 | 1/2008 |
| WO | WO 2009/037610 A2 | 3/2009 |

OTHER PUBLICATIONS

Azoulay et al. Comparison of the Mineral Content of Tap Water and Bottles Waters, (J. Gen. Intern. Med., vol. 16 (2001) 168-175).*
Ford et al. Dietary Magnesium Intake in a National Sample of U.S. Adults, (The Journal of Nutrition, (2003) pp. 2879-2882).*

* cited by examiner

*Primary Examiner* — Anna Skibinsky
(74) *Attorney, Agent, or Firm* — Muncy, Geissler, Olds & Lowe, PLLC (57) ABSTRACT

A mineral water producing method includes the steps of inputting basic data to obtain data about human mineral intake and data about average mineral intake from food; selecting a water supply area to obtain data about mineral intake from daily water intake; selecting an eating habit and a physical/mental condition; inputting personal body weight and calculating mineral intake; setting a daily water intake and calculating a daily mineral supplement; and outputting mineral water. A mineral water producing apparatus includes a water inlet and a water outlet; a first filter being connected at a first end to the water inlet and at a second end to the water outlet; at least one mineral substance container being located between and connected to the second end of the filter and the water outlet; and a controller for controlling the mineral substance container to supply a mineral substance.

4 Claims, 7 Drawing Sheets

| Sex | Age | Recommended calcium intake (DRI) (mg/day) | Average calcium intake from food (mg) |
|---|---|---|---|
| Male | Newborn infant (< 6 months) | 300 | 200 |
| | Infant and toddler (6~12 months) | 400 | 300 |
| | Child (1~10 years old) | 600 | 550 |
| | Adolescence (10~19 years old) | 1200 | 550 |
| | Adult (19~64 years old) | 1000 | 504 |
| | Adult (≥ 65 years old) | 1000 | 622 |
| | | | |
| Female | Newborn infant (< 6 months) | 300 | 200 |
| | Infant and toddler (6~12 months) | 400 | 300 |
| | Child (1~10 years old) | 600 | 503 |
| | Adolescence (10~19 years old) | 1200 | 503 |
| | Adult (19~64 years old) | 1000 | 496 |
| | Adult (≥ 65 years old) | 1000 | 635 |
| | Pregnant woman | 1000 | 496 |

FIG. 4-2

|  | County & City | Average calcium intake from drinking water (mg) |
|---|---|---|
| Area A | Keelung city, Taipei county, Taipei city, Taoyuan county, Miao-Li county, I-Lan county, Hwa-Lien county | 40 |
| Area B | Hsin-Chu county, Hsin-Chu city, Taichung county, Taichung city, Nan-Tou county, Chia-I county, Chia-I city, Tainan county, Tainan city | 65 |
| Area C | Kaohsiung county, Kaohsiung city, Ping-Tong county, Tai-Tung county | 85 |
| Area D | Chang-Hwa county, Yun-Lin county | 100 |
| Other area | Water supplied has been treated by reverse osmosis (RO) or other deionizing processes | 0 |

FIG. 4-3

| Eating Habit | Physical/mental Condition | 4 Factor |
|---|---|---|
| Only vegetables | Hypertension, cardiovascular disorders, osteoporosis, convulsion-prone, anxiety, fatigue, depression | 1.5 |
| | Normal | 1.2 |
| Vegetables, egg, and milk | Overweight, diabetes, hypertension, cardiovascular disorders, osteoporosis, convulsion-prone, anxiety, fatigue, depression | 1.3 |
| | Normal | 1 |
| Prefer vegetables | Overweight, diabetes, hypertension, cardiovascular disorders, convulsion-prone, anxiety, fatigue, depression | 1.3 |
| | Normal | 1 |
| Prefer Meat | Overweight, diabetes, hypertension, cardiovascular disorders, osteoporosis, convulsion-prone, anxiety, fatigue, depression | 1.5 |
| | Normal | 1.3 |

FIG. 5

METHOD AND APPARATUS FOR PRODUCING MINERAL WATER

BACKGROUND

1. Technical Filed

The disclosure relates to a method and apparatus for producing mineral water, and more particularly to a method and software and hardware design of an apparatus for producing mineral water according to user's personal conditions.

2. Technical Art

Mineral substances work in human body like a plurality of meshed gears, and they must exist in the human body in specific ratios to be useful to human health. For example, excessive potassium would cause flat T-wave in electrocardiograph (EKG), deficiency of iron will cause anemia, and excessive sodium will cause hypertension. Therefore, people must take in balanced combination of mineral substances that are suitable for and easily absorbed and metabolized by human body, in order to obtain the functions that are provided by the mineral substances. Vegetables and fruits in daily diet are the main sources of the mineral substances for human body. However, according to many investigation reports, the nutrient contents, particularly mineral substances and vitamins, of currently available vegetables and fruits have obviously reduced. Some possible reasons for the largely reduced nutrient contents of vegetables and fruits include:

(1) New species of vegetables and fruits grow quickly and fail to absorb or synthesize the required types and contents of different nutrition from the soil.

(2) The modern agricultural technologies fail to provide vegetables and fruits with natural growth environment.

(3) According to the Food and Agriculture Organization (FAO) of the United Nations, chemical fertilizers are the main causes leading to serious deficiency of mineral substances in soil.

Dr. Davis, who is a biochemist at University of Texas, USA, has found from the data about the nutrients of 43 vegetables and fruits collected by the US Department of Agriculture on a long-term basis that six types of nutrients in general vegetables and fruits have significantly reduced, including proteins, calcium, phosphorus, iron, vitamin B2 and vitamin C. The percentage of reduction ranges from 6% to 38% for different minerals. According to a report on an investigation conducted under the commission of the Department of Health in Taiwan, the mineral intake from food among male and female of different ages is indeed deficient compared to the recommended mineral intake, and the degree of deficiency is ranged from 10% to 50%. As a matter of fact, the mineral intake that meets the physiological requirements is variable according to persons and living places. However, most people have difficulty in obtaining complete background data and performing complicated calculation based on such data to know the types and quantities of deficient mineral substances that should be daily supplemented to them.

SUMMARY

The producing method for a mineral water includes the steps of inputting basic data to obtain data about human mineral intake and data about average mineral intake from food; selecting a water supply area to obtain data about mineral intake from daily water intake; selecting an eating habit and a physical/mental condition; inputting personal body weight to calculate mineral intake; setting a daily water intake and calculating a daily mineral supplement; and outputting mineral water.

The basic data include sex and age data, and the age data are divided into several groups, including newborn infant, infant and toddler, child, adolescent, adult, aged man, and pregnant woman.

The user's mineral intake can be calculated based on the input data about the user's body weight and the user's daily mineral supplement from the user's daily water intake can be calculated from the following formula: $M=(a-b-c) \times d \times (e/\text{standard reference weight})$ where, a is the recommended human mineral intake selected according to the input sex and age;

b is the average mineral intake from food calculated based on the input sex and age;

c is the mineral intake from daily water intake calculated based on an average quality of water supplied by the selected water supply area;

d is a multiplication factor for calculating the mineral intake according to the selected personal eating habit and specific physical/mental condition; and e is the input user's body weight for calculating the mineral intake.

The user's daily water intake is adapted to the user-set daily water intake, and the calculated mineral supplement is equally added into the user-set daily water intake within a predetermined water discharge time.

When the user's water intake exceeds the user-set daily water intake, the supply of mineral substance is stopped and the water supplied is automatically switched to purified water or other specifically formulated drinking water.

The producing apparatus for a mineral water includes a water inlet and a water outlet; a first filter being connected at a first end to the water inlet and at a second end to the water outlet; at least one mineral substance container being located between and connected to the second end of the filter and the water outlet; and a controller for controlling the mineral substance container to supply a mineral substance.

The mineral water producing apparatus of the embodiment further includes an ultraviolet (UV) irradiator disposed upstream of the water outlet for UV sterilization to ensure the cleanness of the supplied drinking water.

The mineral substance container includes a mineral substance tank, a pump, a second filter, and a gas supply source. The gas supply source is located at a first end of the second filter; a second end of the second filter is connected to a first end of the mineral substance tank; a second end of the mineral substance tank is connected to the pump; and the pump is located between and connected to the second end of the first filter and the water outlet. The mineral substance container can hold a mineral substance for adding into the drinking water under control. In the embodiment, a plurality of mineral substance containers can be included to provide different mineral substances.

BRIEF DESCRIPTION OF THE DRAWINGS

The structure and the technical means adopted by the embodiment to achieve the above and other objects can be best understood by referring to the following detailed description of the preferred embodiments and the accompanying drawings, wherein

FIG. 4-1, 4-2, 4-3 is an exemplified table showing various data in connection with the method and apparatus for producing mineral water according to the embodiment.

DETAILED DESCRIPTION OF THE PREFERRED EMBODIMENTS

Figure 1:
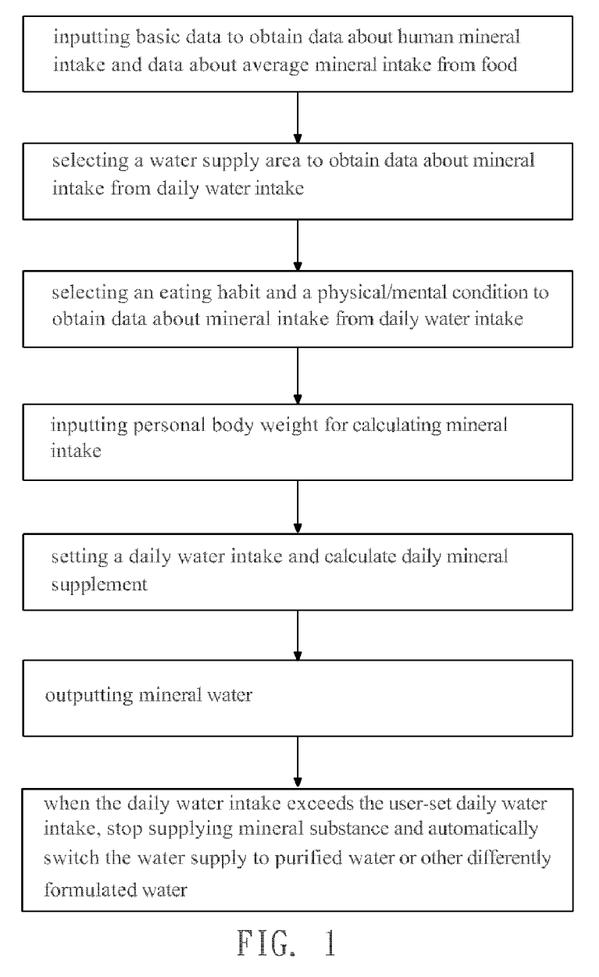
FIG. 1 is a flowchart showing the steps included in a method for producing mineral water according to the embodiment.

Please refer to FIG. 1 that is a flowchart showing the steps included in a method for producing mineral water according to the embodiment. As shown, the method by a microprocessor unit to treat a information includes inputting basic data to obtain data about human mineral intake and data about average mineral intake from food for a user by the microprocessor unit from a database unit; selecting a water supply area to obtain data about mineral intake from daily water intake by the microprocessor unit from a database unit; selecting an eating habit and a physical/mental condition by the microprocessor unit; inputting the user's body weight for calculating required mineral intake by the microprocessor unit from a database unit; setting the user's daily water intake by the microprocessor unit from a database unit; calculating the daily mineral supplement to the user by the microprocessor unit from a database unit; and outputting the mineral water. The basic data includes sex and age. The age data are divided into several groups, including newborn infant, infant and toddler, child, adolescence, adult, aged man, and pregnant woman. The sex data are divided into male and female. Therefore, the types and quantities of mineral substances that should be supplemented to a user can be determined according to the user's basic data. Data about recommended mineral intake for different users can be obtained from related research reports and recommendation from governmental organizations and academic and research institutes. For example, the types and quantities or other related factors of mineral supplement needed by different persons can be obtained from the National Food and Nutrient Reference Intake issued by the Department of Health in Taiwan or other research reports from relevant institutes. Or, data about the average mineral intake from food calculated based on sex and age can also be obtained from the Department of Health and other relevant institutes.

The water supply area has relation with the quality of water available from an area. Therefore, investigation of local water quality must be conducted to derive data about the percentages or quantities of different minerals contained in the locally available water source. Of course, such data can also be obtained from a local water supply company or other research institutes. The water supply area is an important factor for calculating the mineral-content in drinking water. Other factors, such as the user's eating habit, physical/mental condition, and body weight, also have important influences on the user's mineral intake. Generally, data about the mineral intake for persons having different eating habits, physical/mental conditions, and body weights can be obtained from research reports by dietitians. Therefore, according to the embodiment, a user's mineral intake can be calculated based on the input data about the user's body weight and the user's daily mineral supplement from the user's daily water intake can be calculated from the following formula:

$$M=(a-b-c) \times d \times (e/\text{standard reference weight})$$

where, a is the recommended human mineral intake selected according to the input sex and age;

b is the average mineral intake from food calculated based on the input sex and age;

c is the mineral intake from daily water intake calculated based on an average quality of water supplied by the selected water supply area;

d is a multiplication factor for calculating the user's mineral intake according to the selected personal eating habit and physical/mental condition; and e is the input user's body weight for calculating the mineral intake.

According to the embodiment, the user's daily water intake is adapted to the user-set daily water intake (L), and the quantity of mineral supplement obtained from the above calculation is equally added into the user-set daily water intake within a predetermined water discharge time (T). From the above calculation, it is able to obtain the quantity of mineral supplement to meet the recommended mineral intake. In the event the user's water intake exceeds the user-set daily water intake, the supply of mineral substance is stopped and the water supplied is automatically switched to purified water or other differently formulated water.

The above-mentioned steps in the mineral water producing method according to the embodiment, including inputting basic data, selecting the water supply area, selecting eating habit and physical/mental condition, and inputting personal body weight, are not necessarily performed in the order sequence as shown in FIG. 1. That is, in the embodiment, the sequence of the steps of the method can be freely adjusted without influencing the production of the mineral water according to the embodiment. It is the sprit of the embodiment to produce and provide mineral water having mineral content adapted to individual users. Therefore, any and all inventive concepts similar to the spirit of the embodiment are within the protection scope of the embodiment.

The data used in the embodiment for calculation not only refer to, for example, the Recommended Human Mineral Intake issued by the Department of Health in Taiwan, but also include results from compilation and analysis of investigation reports by the Department of Health and water quality analysis reports by water supply companies, so as to establish a human daily mineral intake background database according to the influences of living area, sex, age, eating habit, and physical/mental condition on a person's mineral intake. With the data in this human daily mineral intake background database, when a user inputs personal data, it is able to calculate the deficiency of personal daily mineral intake, that is, the recommended mineral supplement.

Figure 2:
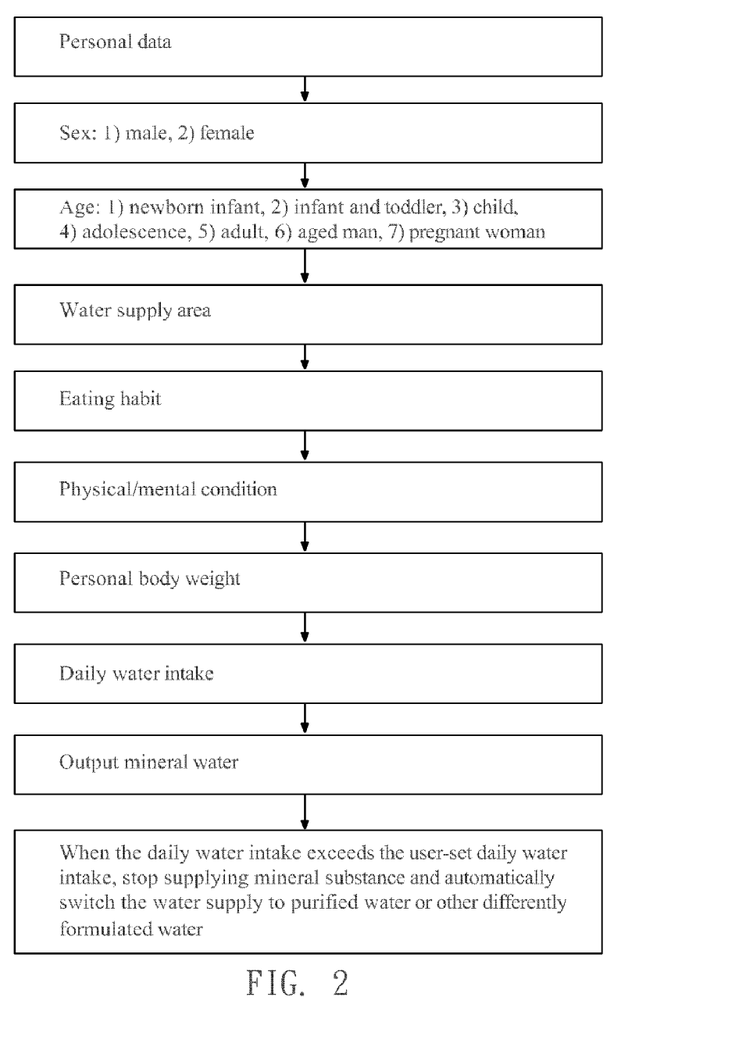
FIG. 2 is a flowchart showing the steps included in a preferred embodiment of the method for producing mineral water according to the embodiment.

FIG. 2 is a flowchart showing the steps included in an embodiment of the mineral water producing method according to the embodiment. In the illustrated embodiment, the mineral to be implemented is calcium. However, it is understood the embodiment is not limited to the supplementation of calcium. As a matter of fact, most of the mineral substances can be supplemented to a user through the mineral water producing method of the embodiment.

The embodiment of the mineral water producing method illustrated in FIG. 2 is based on the supply of calcium supplement and/or other mineral supplement to a user. To do so, basic data about a user is first input in order to obtain data about human mineral intake and data about average mineral intake from food for the user. The basic data includes personal data, such as the user's name, or an identification code (ID) or a representative pattern that is sufficient to represent the user's name. Then, basic data about the user's sex and age are input. For example, in the illustrated embodiment, the selected sex is female, and the selected age is adult. Please refer to the table in FIG. 4-1, 4-2, 4-3. The recommended daily calcium intake is 1000 mg for an adult woman. In the case the user is 25 years old, the average calcium intake from food is 496 mg for the user.

Figure 41:
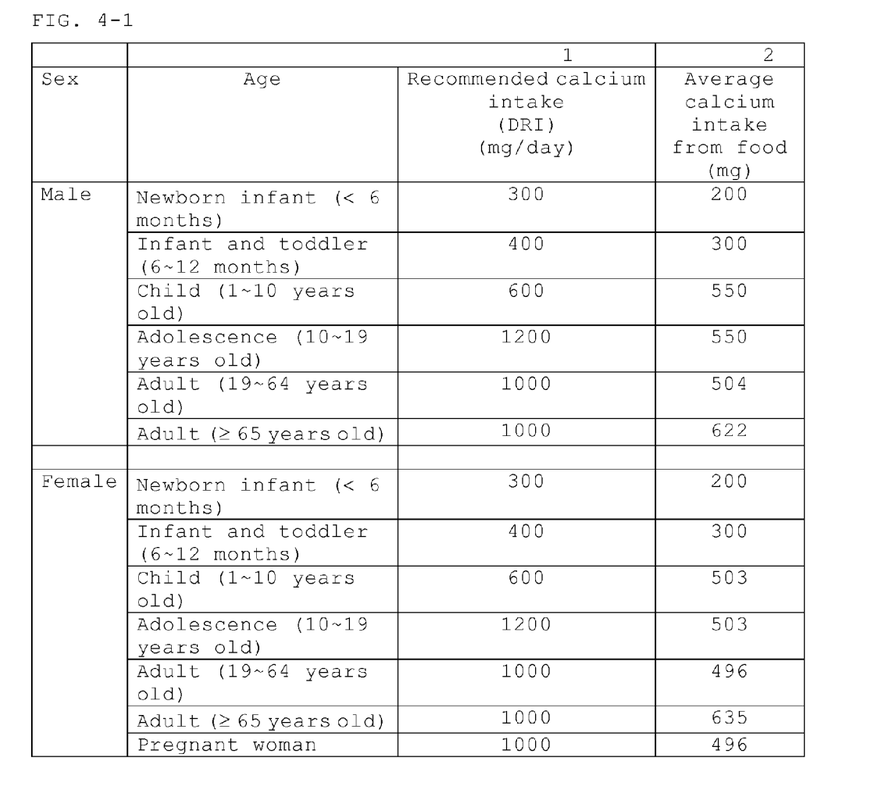
Figure 42:
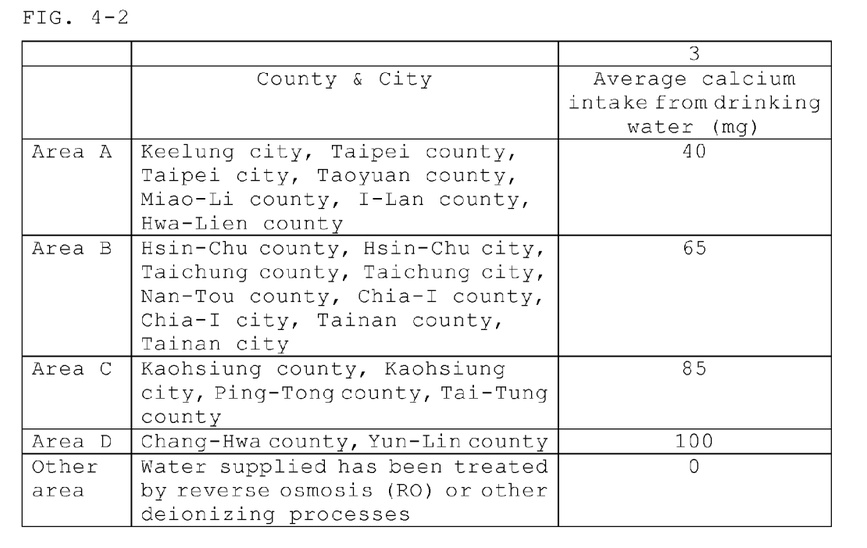
Figure 43:
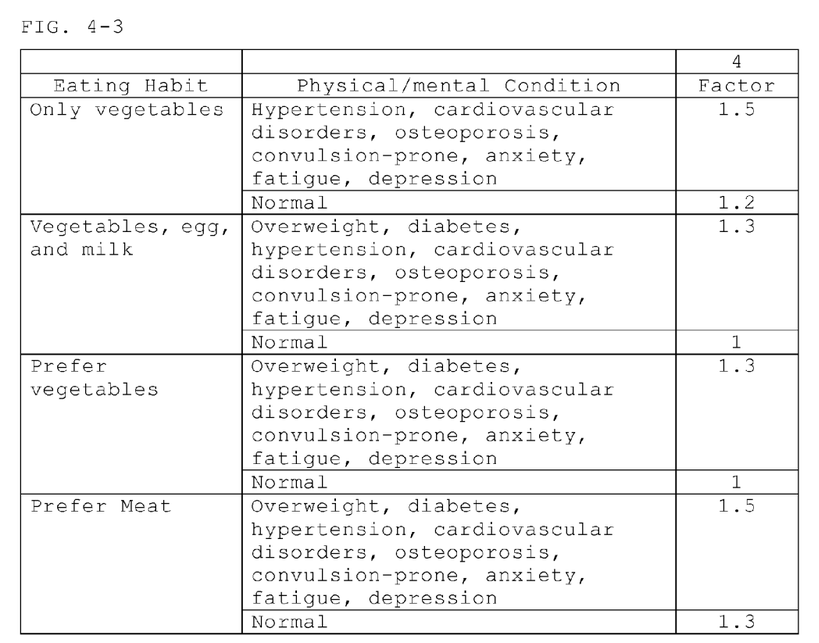

After the basic data have been input, a water supply area is selected, which is Hsin-Chu, for example, in the illustrated embodiment. Please refer to the table in FIG. 4-1, 4-2, 4-3. The calcium content in the water supplied within the area of Hsin-Chu is about 65 mg.

Then, an eating habit and a physical/mental condition are selected, which are, for example, "prefer meat" and "normal", respectively, in the illustrated embodiment. According to the table in FIG. 4-1, 4-2, 4-3, a multiplication factor for the following calculation is set to 1.3 for the selected eating habit and physical/mental condition.

Then, the user's body weight is input to calculate the calcium intake. For example, the input body weight is 55 kg. Then, the user's daily calcium supplement from the drinking water produced by a mineral water producing apparatus according to the embodiment, which will be described later, can be derived by substituting the above relevant values into the formula: $M=(a-b-c) \times d \times (e/\text{standard reference weight})$. That is, $M=(1000-496-65) \times 1.3 \times (55/50)$, with the standard reference weight being 50 kg herein, and the daily calcium supplement (M) from the daily drinking water should be 628 mg. Therefore, when the user-set daily water intake is 1 liter (L), the flow speed of the discharged water is 2 L/min, and the water discharge time is 0.5 min, within which the calculated calcium supplement is to be equally added into the discharged water, and the calcium supplement is presented as a solution having a concentration of 10000 mg/L, then the calcium supplement solution should be added into the drinking water at a flow rate $F(\text{mL/min}) = (628 \text{ mg}/10000 \text{ mg/L}) \times 1000/0.5 \text{ min} = 125.6 \text{ mL/min}$.

In the event the user's water intake exceeds the preset daily water intake of 1 L, for example, the supply of the mineral supplement is stopped and the water supplied is automatically switched to purified water or other differently formulated water.

It is noted the number of items of data shown in the table of FIG. 4-1, 4-2, 4-3 can be increased, and the values of the data shown in the table can be modified when necessary. That is, while the data shown in the table of FIG. 4-1, 4-2, 4-3 are obtained from different sources and have been carefully compiled and analyzed, they are not intended to limit the embodiment in any way.

Figure 5:
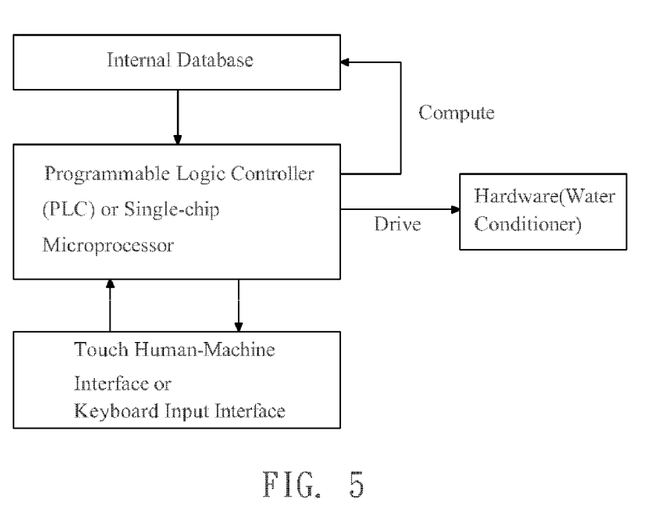
FIG. 5 is a flowchart showing a logic operation/control process of the mineral water producing apparatus according to the present invention.

Please refer to FIG. 5 that is a flowchart showing a logic operation/control process of a mineral water producing apparatus according to the present invention. As shown, in the present invention, the range of different mineral contents in the drinking water discharged from a mineral water producing apparatus of the present invention can be controlled via a programmable logic controller. When basic data about a user is input via a touch human-machine interface or a keyboard input interface, data about human mineral intake and data about average mineral intake from food are obtained from an internal database. The basic data includes personal data, such as the user's name, or an identification code (ID) or a representative pattern that is sufficient to represent the user's name. Then, basic data about the user's sex and age are input via the touch human-machine interface or the keyboard input interface. For example, the selected sex is female, and the selected age is adult. Please refer to the table in FIG. 4-1, 4-2, 4-3. The recommended daily calcium intake is 1000 mg for an adult woman. In the case the user is 25 years old, the average calcium intake from food is 496 mg for the user. The table of FIG. 4-1, 4-2, 4-3 can be built in the internal database. After the basic data have been input, a water supply area, such as Hsin-Chu, can be selected via the touch human-machine interface or the keyboard input interface. Referring to the table in FIG. 4-1, 4-2, 4-3, the calcium content in the water supplied within the area of Hsin-Chu is about 65 mg. Then, an eating habit and a physical/mental condition, such as "prefer meat" and "normal", respectively, can be selected via the touch human-machine interface or the keyboard input interface. According to the selected eating habit and physical/mental condition, the programmable logic controller (PLC) or a single-chip microprocessor calculates the multiplication factor and set the same to 1.3, for example. Then, the user's body weight is input via the touch human-machine interface or the keyboard input interface. According to the input body weight, the PLC or the single-chip microprocessor calculates the calcium intake. For example, the input body weight is 55 kg. Then, the PLC or the single-chip microprocessor calculates the user's daily calcium supplement from the drinking water produced by a mineral water producing apparatus of the present invention, which will be described later, by substituting the above relevant values into the formula: $M=(a-b-c) \times d \times (e/\text{standard reference weight})$. That is, $M=(1000-496-65) \times 1.3 \times (55/50)$, with the standard reference weight being 50 kg herein, and the daily calcium supplement (M) from the daily drinking water should be 628 mg. Therefore, the mineral water producing apparatus (hardware) can be controlled to output the user-set daily water intake of 1 liter (L) at a water discharge speed of 2 L/min and to add the calculated calcium supplement in equal parts to the drinking water discharged within a water discharge time of 0.5 min each time. Supposing the calcium supplement is presented as a solution having a concentration of 10000 mg/L, then the calcium supplement solution should be added to the drinking water at a flow rate $F(\text{mL/min}) = (628 \text{ mg}/10000 \text{ mg/L}) \times 1000/0.5 \text{ min} = 125.6 \text{ mL/min}$. In the event the user's water intake exceeds the preset daily water intake of 1 L, for example, the supply of the mineral supplement is stopped and the water supplied is automatically switched to purified water or other differently formulated water.

The user inputs parameters of personal data, including sex, age, living area, physical/mental condition, body weight, and daily water intake, to the PLC or the microprocessor, and the PLC or the microprocessor will compare these input parameters with data in the internal database to retrieve corresponding values. The PLC or the microprocessor then calculates based on the retrieved corresponding values to generate a mineral supplement value, which is shown on a display of the touch human-machine interface or the keyboard input interface. Meanwhile, the generated mineral supplement value is converted into a pumping flow rate. When the user touches keys on the touch human-machine interface or pushes keys on the keyboard input interface to get drinking water, the PLC or the microprocessor will direct a water conditioner to supply the drinking water and drive a pump to supply the mineral supplement concentrate to the discharged drinking water based on the calculated pumping flow rate.

Figure 3:
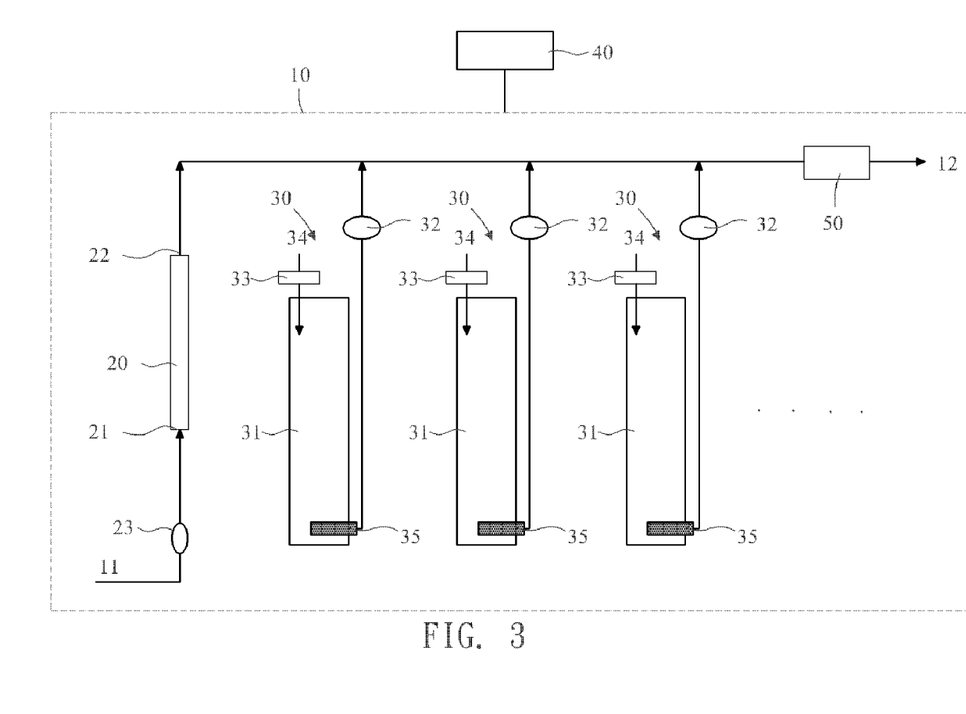
FIG. 3 is a schematic view showing the system of a mineral water producing apparatus according to the embodiment.

Please refer to FIG. 3 that is a schematic view showing the system of a mineral water producing apparatus 10 according to an embodiment. As shown, the mineral water producing apparatus 10 includes a water inlet 11 and a water outlet 12; a first filter 20 having a first end 21 connected to the water inlet 11 and a second end 22 connected to the water outlet 12; at least one mineral substance container 30 located between and connected to the second end 22 of the first filter 20 and the water outlet 12; and a controller 40 for controlling the mineral substance container 30 to supply a mineral solution and actuate a pump 23. Running water or other drinking water is supplied via the water inlet 11 to flow through a flow stabilizer or the pump 23, which stabilizes the in-coming water or supplies a force to transfer the water through the system. The water passed through the first filter 20 is further caused to pass through an ultraviolet (UV) irradiator 50 disposed upstream of the water outlet 12 for UV sterilization, so as to ensure the cleanness of the supplied drinking water. The first filter 20 includes a filtering material, such as a filter net or screen, active carbon, or some other materials for natural filtration. Since the filter 20 is a known skill for removing impurities and bacteria from water, it is not discussed in details herein. However, the use of these filtering materials is also included in the protection scope of the embodiment.

The mineral substance container 30 includes a mineral substance tank 31, a pump 32, a second filter 33, and a gas supply source 34. The gas supply source 34 is located near a first end of the second filter 33, and a second end of the second filter 33 is connected to a first end of the mineral substance tank 31. A second end of the mineral substance tank 31 is connected to the pump 32, and the pump 32 is connected to and located between the second end 22 of the first filter 20 and the water outlet 12. The pump 32 functions to deliver the mineral solution filled in the mineral substance tank 31 to a pipeline between the water inlet 11 and the water outlet 12, so that the mineral solution is added into the water flowed through the first filter 20. When the pump 32 is actuated, air from the gas supply source 34 is pumped through the second filter 33 into the mineral substance tank 31 to balance internal pressure of the mineral substance tank 31. The second filter 33 filters the supplied air to remove impurities and unnecessary substances from the air. In the illustrated embodiment, the mineral substance container 30 includes a plurality of mineral substance tanks 31, in each of which a different mineral supplement solution is filled. It is able to add one single type of mineral solution or a mixture of many types of mineral solutions into the supplied water.

The mineral water producing apparatus 10 is controlled by the controller 40 to operate. The controller 40 programmably controls a database, such as the one shown in the table of FIG. 4-1, 4-2, 4-3, and the steps according to the mineral water producing method of the embodiment, so as to complete the production of desired mineral water.

To prevent the mineral solution filled in the mineral substance tank 31 from containing large-size particles or impurities that must be removed, a third filter 35 is provided in the mineral substance tank 31. In the embodiment, the mineral supplements are extracts and concentrates from natural substances, such as seawater, minerals, or plants. The mineral supplement solution in each mineral substance tank 31 can contain one single type of mineral substance or more than one type of mineral substance. After calculation by specific software, the system is electronically driven to automatically change the flow and the speed of the supplied water to adapt to a user-set daily water intake, and the mineral supplement solution can be automatically added into the supplied drinking water.

The mineral water producing apparatus of the embodiment is advantageously characterized in an operating mode that combines an internally built water quality database and a microcomputer to intelligently and conveniently provide the most reasonable mineral intake for each different user to thereby save the users from the complicated and error-prone manual calculation and operation involved in the daily mineral intake.

It is to provide a mineral water producing apparatus that functions as a smart mineral supplementing water dispenser and has an internally built database to automatically calculate required daily mineral supplement for a user based on basic data input by the user, so that the user can meet the recommended human mineral intake. And, the calculated daily mineral supplement is automatically added into a user-set daily water intake, allowing the user to take in required daily mineral supplement simply via drinking water.

Another is to provide a smart mineral water producing method, in which a required daily mineral supplement for a user is calculated based on basic data, water supply area, eating habit, physical/mental condition, and body weight input by the user, and the calculated daily mineral supplement is added into a user-set daily water intake for the user to meet the required daily mineral supplement.

The mineral water producing apparatus is advantageously characterized in an operating mode that combines an internally built water quality database and a microcomputer to intelligently and conveniently provide the most reasonable mineral intake for each different user to thereby save the users from the complicated and error-prone manual calculation and operation involved in the daily mineral intake.

In brief, the embodiment provides a mineral water producing apparatus that serves as a smart mineral supplementing water dispenser to automatically calculate the required daily mineral supplement for every user based on the user-related basic information, so that the mineral substances taken in by the user can meet the recommended mineral intake for human body. And, the calculated daily mineral supplements are automatically added into the user-set daily drinking water, allowing the user to take in required daily mineral substances simply via drinking water.

What is claimed is:

1. A method for producing mineral water through data computing by a microprocessor unit, comprising:
    inputting a user's basic data via an input interface to obtain data about human mineral intake and data about average mineral intake from food;
    selecting a water supply area via the input interface to obtain data about mineral intake from daily water intake;
    selecting the user's eating habit and a physical and mental condition via the input interface to obtain a multiplication factor for calculating required mineral intake;
    inputting the user's body weight via the input interface, and the microprocessor unit calculating a user's recommended mineral intake;
    setting a user-set daily water intake via the input interface, and the microprocessor unit calculating a daily mineral supplement based on the set daily water intake; and
    outputting mineral water containing the calculated daily mineral supplement,
    wherein the user's recommended mineral intake is calculated based on the input data about the user's body weight and the user's daily mineral supplement from the user-set daily water intake is calculated from the following formula:

$$M=(a-b-c) \times d \times (e/\text{standard reference weight})$$

where,
a is the recommended human mineral intake selected according to input sex and age which are part of the user's basic data;

b is the average mineral intake from food calculated based on the input sex and age;

c is the mineral intake from daily water intake calculated based on an average quality of water supplied by the selected water supply area;

d is a multiplication factor for calculating the user's mineral intake according to the selected personal eating habit and physical and mental condition; and e is the input user's body weight for calculating the mineral intake.

2. The method for producing mineral water as claimed in claim 1, wherein the age data are divided into several groups, including newborn infant, infant and toddler, child, adolescence, adult, aged man, and pregnant woman.

3. The method for producing mineral water as claimed in claim 1, wherein the user's daily water intake is adapted to the user-set daily water intake, and the quantity of mineral supplement obtained from the above calculation is equally added into the user-set daily water intake within a predetermined water discharge time.

4. The method for producing mineral water as claimed in claim 1, wherein, in the event the user's water intake exceeds the user-set daily water intake, the supply of mineral substance is stopped and water supplied is automatically switched purified water.

* * * * *